United States Patent

Librizzi et al.

(10) Patent No.: US 7,803,403 B2
(45) Date of Patent: Sep. 28, 2010

(54) LOW-IRRITATION COMPOSITIONS AND METHODS OF MAKING THE SAME

(75) Inventors: Joseph J. Librizzi, Hillsborough, NJ (US); Russel M. Walters, Philadelphia, PA (US); Michael Fevola, Belle Meade, NJ (US); Krishnan Tamareselvy, Brecksville, OH (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 300 days.

(21) Appl. No.: 11/558,154

(22) Filed: Nov. 9, 2006

(65) Prior Publication Data

US 2008/0112913 A1    May 15, 2008

(51) Int. Cl.
  C11D 1/12    (2006.01)
  C11D 1/66    (2006.01)
  C11D 1/88    (2006.01)
  C11D 3/37    (2006.01)
  A61K 8/37    (2006.01)

(52) U.S. Cl. .............. 424/487; 424/401; 424/70.5; 424/70.16; 424/70.22; 424/70.24; 510/127; 510/155; 510/158; 510/159; 510/426; 510/434; 510/476; 510/477; 510/492

(58) Field of Classification Search ............ 510/127, 510/155, 158, 159, 426, 434, 476, 477, 492; 424/401, 487, 70.5, 70.16, 70.22, 70.24
See application file for complete search history.

(56) References Cited

U.S. PATENT DOCUMENTS

| | | |
|---|---|---|
| 4,110,263 A | 8/1978 | Lindemann et al. |
| 4,186,113 A | 1/1980 | Verdicchio et al. |
| 4,215,064 A | 7/1980 | Lindemann et al. |
| 4,233,192 A | 11/1980 | Lindemann et al. |
| 4,256,611 A | 3/1981 | Egan et al. |
| 4,263,178 A | 4/1981 | Guth |
| 4,372,869 A | 2/1983 | Lindemann et al. |
| 4,380,637 A | 4/1983 | Lindemann et al. |
| 4,382,036 A | 5/1983 | Lindemann et al. |
| 4,443,362 A | 4/1984 | Guth et al. |
| 4,552,685 A | 11/1985 | Kernstock et al. |
| 4,617,414 A | 10/1986 | Lukenbach et al. |
| 4,726,915 A | 2/1988 | Verdicchio |
| 4,948,576 A | 8/1990 | Verdicchio et al. |
| 5,004,557 A * | 4/1991 | Nagarajan et al. ........... 510/337 |
| 5,373,044 A | 12/1994 | Adams et al. |
| 5,661,189 A | 8/1997 | Grieveson et al. |

(Continued)

FOREIGN PATENT DOCUMENTS

DE    19818410 A1    10/1999

(Continued)

OTHER PUBLICATIONS

U.S. Appl. No. 10/922,668, filed Aug. 19, 2004, Joseph Librizzi.

(Continued)

*Primary Examiner*—Brian P Mruk

(57) ABSTRACT

Provided are compositions comprising a low molecular weight, non-crosslinked, linear acrylic copolymer and at least one surfactant selected from the group consisting of anionic surfactants, amphoteric surfactants, and combinations of two or more thereof, and methods of using such compositions.

16 Claims, 3 Drawing Sheets

U.S. PATENT DOCUMENTS

| | | | |
|---|---|---|---|
| 5,792,739 | A | 8/1998 | He et al. |
| 5,876,705 | A | 3/1999 | Uchiyama et al. |
| 6,001,344 | A | 12/1999 | Villa et al. |
| 6,172,019 | B1 | 1/2001 | Dehan et al. |
| 6,433,061 | B1 | 8/2002 | Marchant et al. |
| 6,642,198 | B2 | 11/2003 | Pfiederer et al. |
| 6,737,394 | B2 | 5/2004 | Shana's et al. |
| 7,098,180 | B2 | 8/2006 | Ganopolsky et al. |
| 7,157,414 | B2 | 1/2007 | LiBrizzi et al. |
| 2002/0123438 | A1 | 9/2002 | Pfiederer et al. |
| 2003/0026775 | A1 | 2/2003 | Marchesi et al. |
| 2003/0103929 | A1* | 6/2003 | Maubru .................. 424/70.16 |
| 2003/0108578 | A1 | 6/2003 | Maubru |
| 2003/0147827 | A1 | 8/2003 | Decoster et al. |
| 2003/0171230 | A1 | 9/2003 | Shana'a et al. |
| 2004/0001792 | A1 | 1/2004 | Biatry |
| 2004/0042990 | A1 | 3/2004 | Biatry |
| 2004/0047824 | A1 | 3/2004 | Biatry |
| 2004/0052739 | A1 | 3/2004 | Biatry |
| 2004/0091441 | A1 | 5/2004 | Heike et al. |
| 2004/0175342 | A1 | 9/2004 | Biatry |
| 2005/0070453 | A1 | 3/2005 | Librizzi et al. |
| 2007/0017553 | A1 | 1/2007 | Neplenbroek et al. |

FOREIGN PATENT DOCUMENTS

| | | |
|---|---|---|
| DE | 100 57 925 A1 | 5/2002 |
| DE | 10057925 A | 5/2002 |
| EP | 1 192 938 A2 | 4/2002 |
| EP | 1 374 852 A1 | 1/2004 |
| EP | 1374852 A | 1/2004 |
| WO | WO 03/074021 A | 9/2003 |
| WO | WO 03/074021 A1 | 9/2003 |
| WO | WO 03/084499 A | 10/2003 |
| WO | WO 03/084499 A2 | 10/2003 |
| WO | WO 2004/006870 A | 1/2004 |
| WO | WO 2004/006870 A2 | 1/2004 |

OTHER PUBLICATIONS

U.S. Appl. No. 10/959,272, filed Oct. 4, 2004, Arup Bhattacharyya.

Bernhofer, et al., *Toxicology in Vitro*, The Influence of the Response of Skin Equivalent Systems to Topically Applied Consumer Products by Epithelial-Mesenchymal Interactions 219-229 (1999).

Carbopol® Aqua SF-1 Polymer, Brilliant Gold Pearlized 2-In-1 Conditioning Shampoo Formulation, Noveon, Inc. CASF1-001, Dec. 2000.

Carbopol® Aqua SF-1 Polymer, Pearlized 2-in-1 Conditioning Shampoo formulation, Noveon, Inc., CASF1-002, Nov. 19, 2001.

Carbopol® Aqua SF-1 Polymer, Clear Shampoo Formulation, Noveon, Inc., CASF1-003, Dec. 2000.

Carbopol® Aqua SF-1 Polymer, Bath Gel with Vitamin E Moisturizing Beads Formulation, Noveon, Inc., CASF1-004, Dec. 2000.

Carbopol® Aqua SF-1 Polymer, Pearlized Mild Body Wash Formulation, Noveon, Inc., CASF1-005, Nov. 19, 2001.

Carbopol® Aqua SF-1 Polymer, Clear Bath Gel (High Betaine) Formulation, Noveon, Inc., CASF1-006, Dec. 2000.

Carbopol® Aqua SF-1 Polymer, Anti-Dandruff Shampoo Formulation, Noveon, Inc., CASF1-007, Dec. 2000.

Carbopol® Aqua SF-1 Polymer, Clear Shampoo/Bath Gel with Beads Formulation, Noveon, Inc., CASF1-008, Mar. 29, 2002.

Carbopol® Aqua SF-1 Polymer, Salicylic Acid Shampoo Formulation, Noveon, Inc., CASF1-009, Dec. 2000.

Carbopol® Aqua SF-1 Polymer, Salicylic Acid Facial Scrub Formulation, Noveon, Inc., CASF1-010, Feb. 25, 2002.

Carbopol® Aqua SF-1 Polymer, Temporary Hair Color shampoo (Medium Brown) Formulation, Noveon, Inc., CASF1-011, Dec. 2000.

Carbopol® Aqua SF-1 Polymer, Antibacterial Liquid Hand Soap with suspended Beads Formulation, Noveon, Inc., CASF1-012, Dec. 2000.

Carbopol® Aqua SF-1 Polymer, Clear Facial Cleanser Formulation, Noveon, Inc., CASF1-013, Dec. 2000.

Carbopol® Aqua SF-1 Polymer, Clear Hydrating Body Wash with Suspended Beads Formulation, Noveon, Inc., CASF1-014, Nov. 19, 2001.

Carbopol® Aqua SF-1 Polymer, Sprayable d-Limonene Waterless Hand Cleaner Formulation, Noveon, Inc., CASF1-015, Jan. 2001.

Carbopol® Aqua SF-1 Polymer, Body Lotion Formulation, Noveon, Inc., CASF1-016, Dec. 2000.

Carbopol® Aqua SF-1 Polymer, Facial Cream Formulation, Noveon, Inc., CASF1-017, Dec. 2000.

Carbopol® Aqua SF-1 Polymer, Alpha Hydroxy Acid Cream Formulation, Noveon, Inc., CASF1-018, Dec. 2000.

Carbopol® Aqua SF-1 Polymer, Pearlized 3-In-1 Conditioning Shampoo Formulation, Noveon, Inc., CASF1-019, Nov. 19, 2001.

Carbopol® Aqua SF-1 Polymer, Clear Shampoo with Microcapsules Formulation, Noveon, Inc., CASF1-020, Dec. 2000.

Carbopol® Aqua SF-1 Polymer, Clear Baby Shampoo Formulation, Noveon, Inc., CASF1-021, Dec. 2000.

Carbopol® Aqua SF-1 Polymer, Economy Pearlized 3-in-1 Conditioning Shampoo Formulation, Noveon, Inc., CASF1-022, Jan. 2001.

Clear Conditioning Shampoo Using Ultrasil™ Q-Plus and Ultrasil™ A-23 Silicones, Noveon, Inc., SIL-019, Dec. 12, 2002.

Clear Bath Gel (High Betaine) Using Carbopol® Aqua SF-1 Polymer, Noveon, Inc., CASF1-024EU, Feb. 10, 2003.

Clear Shampoo/Bath Gel with Beads Using Carbopol® Aqua SF-1 Polymer, Noveon, Inc., CASF1-025EU, Feb. 26, 2003.

Brilliant Gold Pearlized 2-in-1 Conditioning Shampoo Using Carbopol® Aqua SF-1 Polymer, Noveon, Inc., CASF1-026EU, Feb. 26, 2003.

Ethnic Hair Moisturizing Cream With Ultracas™ G-20, Noveon, Inc., SIL-0002, Jun. 28, 2001.

Antibacterial Hand Wash with Moisturizers Using Ultrasil™ DW-18 Silicone, Noveon, Inc., SIL-0005, Mar. 1, 2002.

Mild Conditioning Cream Shampoo, Noveon, Inc., SIL-0017, Dec. 12, 2002.

Moisturizing Shampoo for Ethnic Hair, Noveon, Inc., SIL-0020, Feb. 26, 2003.

Aveeno® Stress Relief Foaming Bath Formulation, Johnson & Johnson Consumer Companies, Inc., 2003.

Aveeno® Daily Moisturizing Foaming Bath Formulation, Johnson & Johnson Consumer Companies, Inc., 2003.

Aveeno® Positively Radiant™ Cleanser Formulation, Johnson & Johnson Consumer Companies, Inc., 2003.

Johnson's® Softwash™ Baby Shampoo Formulation, Johnson & Johnson Consumer Companies, Inc., 2002.

Johnson's® Softwash™ Baby Wash Formulation, Johnson & Johnson Consumer Companies, Inc., 2002.

Johnson's® Soothing Skin Baby Bath Formulation, Johnson & Johnson Consumer Companies, Inc., 2001.

Invittox Protocol No. 86, "The Trans-Epithelial Permeability (TEP) Assay," (May 1994).

Moore, et al., Challenging the surfactant monomer skin penetration model: Penetration of sodium dodecyl sulfate micelles into the epidermis (Journal of Cosmetic Science), Nov. 15, 2002, pp. 29-45.

Moore, et al., Penetration of mixed micelles into the epidermis: Effect of mixing sodium dodecyl sulfate with dodecyl hexa (ethylene oxide) (Journal of Cosmetic Science), 54, 2003, pp. 143-159.

Lubrizol, Molecular Weight of Carbopol® *Polymers, Oct. 15, 2007, pp. 1-3, Lubrizol Advanced Materials, Inc., Cleveland, Ohio.

European Search Report dated Dec. 21, 2004 for EP appln. 04254988.1.

European Search Report dated Dec. 21, 2004 for EP appln. 04254989.9.
European Search Report dated Dec. 21, 2004 for EP appln. 04254987.3.
European Search Report dated Dec. 21, 2004 for EP appln. 04254990.7.
International Search Report dated Dec. 17, 2004 for PCT/US04/27317.

Chevron Phillips, Specialty Chemicals, "Polyanhydride Resins" [online] 2009 [retrieved on Sep. 25, 2009] from http://www.epchem.com/enu/specialtychemicalspolyanhydrideresins.asp.
Chevron Phillips, MSDS "PA-18" [online] Nov. 8, 2005 [retrieved on Sep. 25, 2009] from http://www.cpchem.com/enu/msds_unsecured/ImportPE0090MSDSOENGLISH_AENGLISHAN.pdf.

* cited by examiner

LOW-IRRITATION COMPOSITIONS AND METHODS OF MAKING THE SAME

FIELD OF INVENTION

The present invention relates to compositions having low irritation characteristics in combination with one or more additional characteristics, for example, relatively high clarity, relatively high foaming, and/or combinations thereof, as well as methods of making and using such compositions.

DESCRIPTION OF THE RELATED ART

Synthetic detergents, such as cationic, anionic, amphoteric, and non-ionic surfactants, are used widely in a variety of detergent and cleansing compositions to impart cleansing properties thereto. In addition, in certain compositions (e.g. personal care compositions such as shampoos, washes, etc.), it may be desirable to use combinations and levels of surfactants sufficient to achieve relatively high levels of foam volume and/or foam stability.

However, as is recognized in the art, synthetic detergents tend to be irritating to the skin and eyes. Thus, as levels of such detergents are increased in attempts to increase cleansing and foaming properties associated with certain compositions, the irritation associated with such compositions also tends to increase, making them undesirable for use on or near the skin and/or eyes.

Certain attempts to produce milder cleansing compositions have included combining relatively low amounts of anionic surfactants (which tend to be relatively high-foaming but also relatively highly irritating), with relatively lower irritating surfactants such as nonionic and/or amphoteric surfactants. See, e.g. U.S. Pat. No. 4,726,915. Another approach to producing mild cleansing compositions is to associate the anionic surfactants with amphoteric or cationic compounds in order to yield surfactant complexes. See, e.g., U.S. Pat. Nos. 4,443,362; 4,726,915; 4,186,113; and 4,110,263. Disadvantageously, mild cleansing compositions produced via both of such methods tend to suffer from relatively poor foaming and cleansing performance.

Applicants have further recognized that for certain uses it is desirable for cleansing compositions to be relatively clear. In particular, clear compositions are often used advantageously to provide an aesthetic indication of purity to the consumer. However, applicants have recognized that the use of various ingredients in conventional cleansers, including, for example, polymeric thickeners, tend to result in cloudy or opaque compositions. Thus, it is not readily predictable which combinations of polymers, surfactants and other optional ingredients may be combined to create compositions that are suitable for use as cleansers and also exhibit high clarity.

Accordingly, applicants have recognized the need for compositions that are not only mild to the skin and/or eyes, but additionally exhibit relatively high clarity, desirable foam properties and/or other desirable aesthetic properties.

SUMMARY OF THE INVENTION

The present invention provides mild cleansing compositions and methods of reducing the irritation associated with a variety of personal care compositions, which compositions and methods overcome the disadvantages of the prior art. In particular, according to certain preferred embodiments of the present invention, applicants have discovered advantageously that non-crosslinked, linear acrylic copolymer materials capable of binding surfactant thereto can be used to produce personal care compositions exhibiting surprisingly low irritation to the skin and/or eyes. In certain embodiments, the mild compositions of the present invention additionally exhibit relatively high clarity, high-foaming/foam stability properties, and/or unique viscosity characteristics, as compared to compositions comprising comparable, polymeric materials.

According to one aspect, the present invention provides for compositions comprising a non-crosslinked, linear acrylic copolymer and at least one surfactant selected from the group consisting of anionic surfactants, amphoteric surfactants, nonionic surfactants and combinations of two or more thereof.

According to another aspect of the present invention, provided are methods of reducing the irritation associated with a composition comprising an anionic, amphoteric, and/or non-ionic surfactant, the method comprising combining a non-crosslinked, linear acrylic copolymer material with at least one surfactant selected from the group consisting of anionic surfactants, amphoteric surfactants, and combinations of two or more thereof.

According to yet another aspect of the present invention, provided are methods of cleansing a portion of the human body with reduced irritation thereto comprising the step of contacting the body of a mammal with a reduced irritation composition comprising an anionic and/or amphoteric surfactant and a non-crosslinked, linear acrylic copolymer material.

DESCRIPTION OF PREFERRED EMBODIMENTS

As used herein the term "low molecular weight" polymer refers to a polymer having a number average molecular weight ($M_n$) as measured by gel permeation chromatography (GPC) calibrated with a poly(methyl methacrylate) (PMMA) standard of about 100,000 or less. In certain preferred embodiments, low-molecular weight polymers are those having molecular weight ranges of from about 5,000 to about 80,000 $M_n$, more preferably from about 10,000 to about 50,000 $M_n$, and more preferably between about 15,000 and 40,000 $M_n$.

Figure 1:
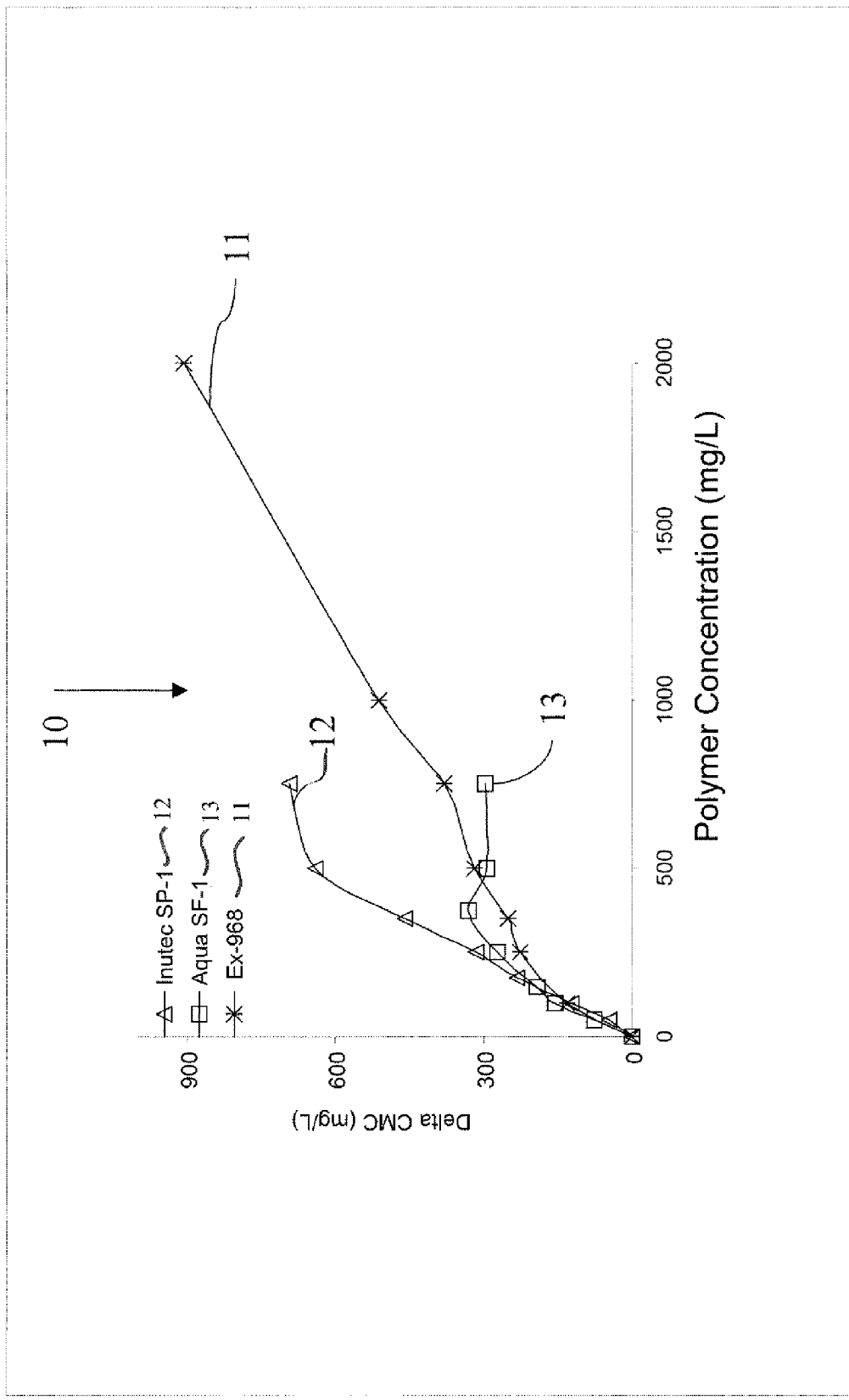
FIG. 1 is a graphical depiction of the relative ability of polymers of one embodiment of the present invention, a comparable low-molecular weight polymer, and a comparable higher molecular weight polymer, to associate surfactants thereto.

Applicants have herein discovered that the compositions of the present invention exhibit a unique and unexpected combination of properties including relatively low irritation, and preferably including both relatively low irritation and relatively high clarity. In particular, with respect to low-irritation, applicants have measured the relative efficiency in binding surfactant, C90, Delta CMC, TEP, and Delta TEP (as defined herein) of the compositions of the present invention and discovered that they tend to be significantly better than compositions comprising comparable commercially available polymers having a relatively high molecular weight, and at least as good as compositions comprising other low molecular weight polymers. For example, shown in FIG. 1 is a graph 10 of the relative ability of polymers of one embodiment of the present invention (curve 11), a comparable low-molecular weight polymer (sold under the Tradename "Inutec SP-1" by Orafti, curve 12), and a comparable higher molecular weight polymer (sold as Carbopol Aqua SF-1 by Noveon, curve 13), to associate surfactants thereto. Such ability was measured by calculating the Delta CMC associated with the polymer and surfactant using the Forward Titration Tensiomtry Test, as described below wherein higher Delta CMC indicates higher association of surfactant to polymer, and the Delta CMC plotted as a function of polymer concentration to illustrate the relative efficiency of the polymers of the present invention in associating the surfactant. As seen in FIG. 1, the polymer of the present invention tends to associate surfactant efficiently at relatively low concentrations and, in particular, tends to be significantly and unexpectedly efficient in associating surfactant at relatively higher concentrations as compared to the comparative polymeric materials shown.

Although applicants do not wish to be bound by or to any particular theory of operation, it is believed that the polymeric materials suitable for use in the instant methods act to reduce the irritation associated with personal care compositions, at least in part, by binding surfactant (free (unbound) surfactant molecules and/or, especially, surfactant free (unbound) micelles) thereto to reduce the concentration of irritation-causing free micelles available in the composition to irritate the skin and/or eyes. That is, applicants have recognized that the relative amounts of surfactant free micelles contained in a particular composition affect the relative irritation to the skin and/or eyes associated with that composition, wherein higher amounts of free micelles tend to cause higher levels of irritation and lower levels of free micelles tends to cause less irritation. By binding surfactant and/or surfactant micelles thereto, the polymeric materials reduce the concentration of unbound surfactant micelles in a composition and allow for a higher concentration of surfactant to be added to the composition before free micelles are formed and/or before a particular level of irritation is achieved. This desirable shift in the concentration of surfactant required prior to the formation of free micelles is illustrated further in FIG. 2.

Figure 2:
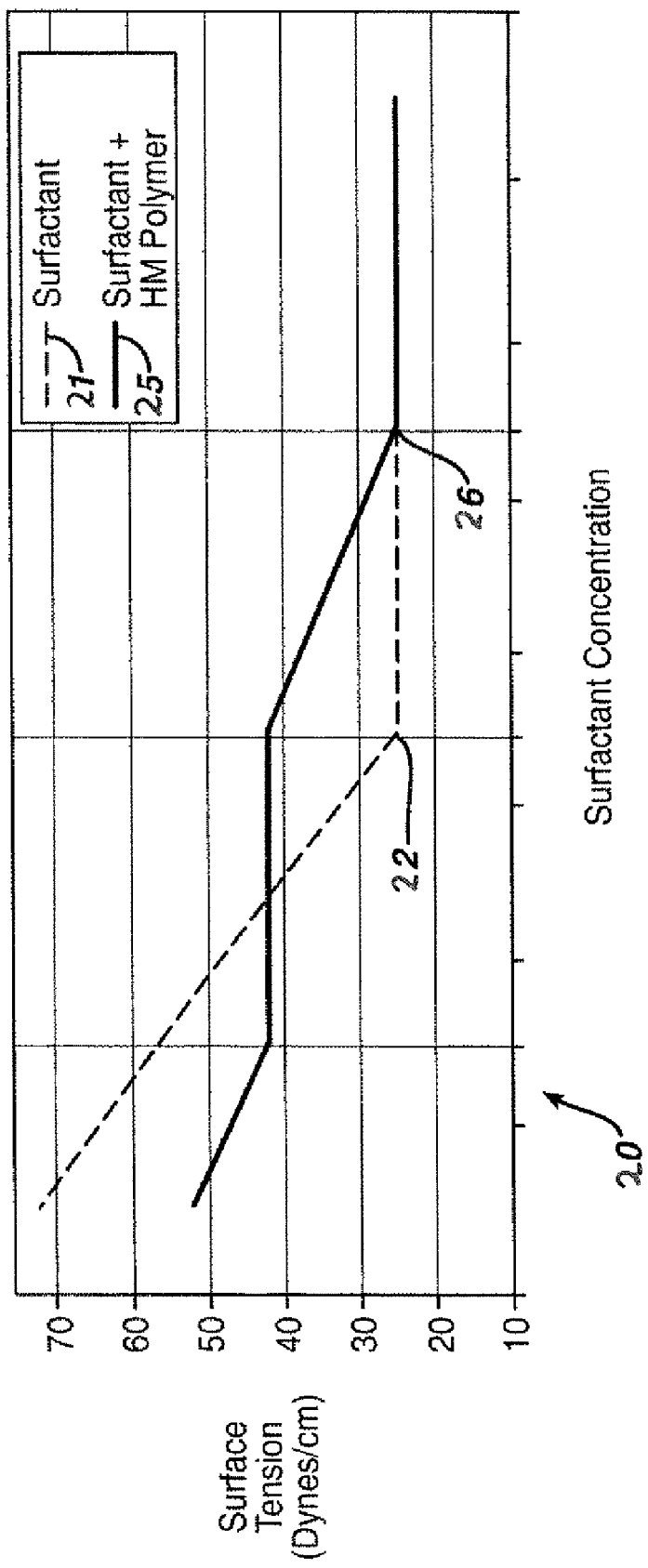
FIG. 2 is a graphical depiction of the idealized tensiometry data associated with the addition of anionic surfactant to two solutions.

FIG. 2 is a graph 20 showing the idealized surface tension data curves associated with the addition of anionic surfactant to two compositions, a composition comprising a polymeric material of the present invention and a comparable composition composition free of polymeric material. Curve 21 shows the change in surface tension, measured via conventional tensiometry techniques (examples of which are described hereinbelow), of a composition free of polymeric material as increasing levels of anionic surfactant are added thereto. Curve 25 shows the change in surface tension of a composition comprising polymeric material as increasing levels of anionic surfactant are added thereto. In curve 21, as surfactant is added to solution, the surfactant tends to populate the liquid/air interface, thus reducing the surface tension of the solution, until essentially the entire surface area is filled. After this point, hereinafter the "critical micelle concentration (CMC)" of surfactant, point 22, essentially all surfactant added to the composition forms free micelles in solution, which formation does not have an appreciable affect on the surface tension of the solution, but tends to increase the irritation associated with the composition. By comparison, as shown in curve 25, as anionic surfactant is added to a solution comprising a polymeric material of the present invention, the surfactant both aligns itself on the liquid/air interface and binds to the polymeric material until the CMC, point 26, shifted to a significantly higher surfactant concentration as compared to curve 21, at which point the surfactant added tends to form free micelles.

In light of the above, applicants have recognized that one measure of the efficacy of a particular low molecular weight polymeric material in binding surfactant thereto may be expressed as the "Delta CMC" achieved by combining the polymeric material with an anionic surfactant to form a reduced irritation composition. A "Delta CMC" as used herein is defined as the number obtained by: (a) determining the CMC for: (i) a particular composition of the present invention comprising anionic surfactant and polymeric material, and (ii) the "comparable composition" of the composition in (i), which CMC values are determined using either the Forward or Reverse Titration Tensiomtry Test procedures defined in the Examples below; and (b) subtracting the CMC value obtained for composition (ii) from the value obtained for composition (i). As used herein, the "comparable composition" of a particular composition comprising anionic surfactant and polymeric material means a composition which consists of the same components in the same relative weight percents as the anionic surfactant/polymeric material composition with the exception that the polymer of the anionic surfactant/polymeric material composition is replaced in the comparable composition with the same relative weight percent of water. For example, the comparable composition for an anionic surfactant/polymeric material composition consisting of 7% anionic surfactant, 15% amphoteric surfactant, 5% low molecular weight polymer, 5% glycerin, and 68% water (wherein all percents are by weight based on the total weight of the composition) is a composition consisting of 7% anionic surfactant, 15% amphoteric surfactant, 5% glycerin, and 73% water. By way of further example, the capability of a particular polymer material to bind a particular surfactant thereto in accord with the present invention may also be readily determined by measuring the CMC values of a composition comprising just the polymeric material and the surfactant in solution (for example, 12% surfactant/3% low molecular weight polymer/85% water) and a comparable composition comprising just the surfactant in solution (for example, 12% surfactant/88% water) and subtracting the latter from the former to get a Delta CMC.

Applicants have now discovered that combinations of non-crosslinked, linear acrylic copolymer materials with anionic, nonionic and/or amphoteric surfactants, preferably at least one anionic and/or amphoteric surfactants, tend to result in significant positive delta CMC (and thus significant reduction in irritation) that is at least as good, if not better than the delta CMC (and reduction of irritation) associated with the addition of comparative polymers. In certain embodiments, it is preferred to select a non-crosslinked, linear acrylic copolymer material for use in the present methods such that the Delta CMC measured using the Reverse Titration Tensiomtry Test associated with the resulting reduced irritation composition is a positive value. In certain more preferred embodiments, the non-crosslinked, linear acrylic copolymer material is selected to achieve a reduced irritation composition having a Delta CMC measured using the Reverse Titration Tensiomtry Test of about +80 or greater, more preferably, about +100 or greater, even more preferably of about +120 or greater, even more preferably of about +200 or greater, and even more preferably of about +300 or greater. In certain other preferred embodiments, the non-crosslinked, linear acrylic copolymer polymer for use in the present invention is one which results in a Delta CMC measured using the Reverse Titration Tensiomtry Test of about +400 or greater, more preferably, about +450 or greater, even more preferably of about +500 or greater, and even more preferably of about +600 or greater.

Applicants have recognized that the "TEP value" associated with a particular composition, which value is measured conventionally via the Trans-Epithelial Permeability Test ("TEP Test") as set forth in the Invittox Protocol Number 86 (May 1994) incorporated herein by reference and described in further detail in the Examples below, has a direct correlation to the irritation to the skin and/or eyes associated with the composition. More specifically, a higher TEP value of a composition tends to indicate less irritation to the skin and eyes associated therewith as compared to a composition having a lower TEP value, which composition tends to cause higher levels of irritation to the skin and/or eyes. Applicants have recognized that the present methods are suitable for producing personal care compositions having relatively high TEP values/lower irritation associated therewith. For example, in certain embodiments, the present methods produce compositions having a TEP value of at least about 1.5 or greater. In certain more preferred embodiments, the composition produced according to the present methods exhibit a TEP value of at least about 2 or greater, more preferably, at least about 2.5 or greater, even more preferably, at least about 3 or greater, and still more preferably, at least about 3.5 or greater. In certain particularly preferred embodiments, the compounds exhibit a TEP value of at least about 4.0 or greater, and even more preferably, about 4.5 or greater.

Furthermore, to determine when, and to express the degree to which, a composition comprising an anionic surfactant and polymeric material produced via the present methods exhibits reduced irritation in comparison to a comparable composition free of the polymeric material, applicants herein define the term "Delta TEP" of a composition of the present invention as the value obtained by: (a) measuring the TEP values of: (i) the composition of the present invention comprising an anionic surfactant and polymeric material and (ii) the comparable composition for such composition; and (b) subtracting the TEP value of the comparable composition from the TEP value for the anionic surfactant/polymeric material composition. Certain preferred reduced irritation compositions of the present invention include those having a Delta TEP of at least about +0.5. Certain more preferred reduced irritation compositions include those having a Delta TEP of at least about +0.75, and more preferably at least about +1. Certain particularly preferred reduced irritation compositions include those having a Delta TEP that is at least about +1.2, more preferably at least about +1.5, and more preferably at least about +1.8.

As indicated above, applicants have discovered that a positive shift in CMC correlates to a higher TEP and lower irritation associated with a composition. Accordingly, as used herein the term "reduced irritation composition" refers generally to a composition comprising an anionic surfactant and one or more polymeric materials capable of binding surfactant thereto, which composition has a positive Delta CMC measured using the Reverse Titration Tensiomtry Test and a positive Delta TEP value (i.e. the composition has higher TEP value than its comparable composition), measured via the Invittox Protocol incorporated herein. Certain preferred reduced irritation compositions exhibit combinations of the preferred Delta CMC and Delta TEP values disclosed above (and include any combinations of preferred, more preferred, and even more preferred values of at least one Delta CMC and at least one Delta TEP).

Applicants have further recognized that the present invention allows for the production of compositions that exhibit not only reduced irritation, but also desirable clarity, rheology and/or foaming properties. In particular, applicants have measured the clarity of the present compositions (via the Clarity Test described herein below, wherein a higher percent transmittance relates to a composition that is clearer than a composition having a lower percent transmittance) and the turbidity of the compositions (via the Turbidity Test described herein below, wherein a lower NTU value relates to a composition that is clearer than a composition having a higher NTU value) and have discovered unexpectedly that such compositions have an unexpected and relatively high clarity as compared to comparable compositions comprising other low molecular weight polymers and/or high molecular weight polymers. For example, applicants have discovered that in certain embodiments the present compositions exhibit a clarity that is up to about 2.6 times or more greater than comparable compositions. In certain preferred embodiments, the present compositions exhibit a clarity as measured via the Clarity Test of at least about 90% transmittance. In certain more preferred embodiments, the present compositions exhibit a clarity at least about 93% transmittance, more preferably at least about 95% transmittance, more preferably at least about 97% percent transmittance, and in certain preferred embodiments at least about 98%. In certain embodiments, the present compositions exhibit a turbidity that is less than about 100 NTU, more preferably less than about 50 NTU, more preferably less than about 20 NTU, more preferably less than about 10 NTU, and in certain preferred embodiments less than about 5 NTU.

In addition, applicants have discovered that while certain higher molecular weight polymers tend to increase the viscosity and the yield point associated with a composition as more polymer is added, the polymers of the present invention tend to have relatively small effect on the rheology of the compositions to which they are added. Accordingly, in certain embodiments, higher amounts of the present polymers may be added to more significantly reduce irritation without producing a composition that is too viscous for effective personal use.

The polymeric material for use in the present compositions is preferably a composition suitable for associating anionic and/or amphoteric surfactant thereto and is a non-crosslinked, linear acrylic copolymer that mitigates the ocular and dermal irritation typically associated with surfactant systems without substantially increasing viscosity build. The non-crosslinked, linear polymers are preferably of low molecular weight having a number average molecular weight of 100,000 or less as measured by gel permeation chromatography (GPC) calibrated with a poly(methyl methacrylate) (PMMA) standard (as used herein, unless otherwise specified, all number average molecular weights ($M_n$) refer to molecular weight measured in such manner). The copolymeric mitigant is polymerized from at least two monomeric components. The first monomeric component is selected from one or more $\alpha,\beta$-ethylenically unsaturated monomers containing at least one carboxylic acid group. This acid group can be derived from monoacids or diacids, anhydrides of dicarboxylic acids, monoesters of diacids, and salts thereof. The second monomeric component is hydrophobically modified (relative to the first monomeric component) and is selected from one or more $\alpha,\beta$-ethylenically unsaturated non-acid monomers containing a $C_1$ to $C_9$ alkyl group, including linear and branched $C_1$ to $C_9$ alkyl esters of (meth)acrylic acid, vinyl esters of linear and branched $C_1$ to $C_{10}$ carboxylic acids, and mixtures thereof. In one aspect of the invention the second monomeric component is represented by the formula:

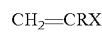

wherein R is hydrogen or methyl; X is —C(O)OR¹ or —OC(O)R²; R¹ is linear or branched $C_1$ to $C_9$ alkyl; and R² is hydrogen or linear or branched $C_1$ to $C_9$ alkyl. In another aspect of the invention R¹ and R² is linear or branched $C_1$ to $C_8$ alkyl and in a further aspect R¹ and R² are linear or branched $C_2$ to $C_5$ alkyl.

Exemplary first monomeric components include (meth)acrylic acid, itaconic acid, citraconic acid, maleic acid, fumaric acid, crotonic acid, aconitic acid, and mixtures thereof. Exemplary second monomeric components include ethyl (meth)acrylate, butyl (meth)acrylate, 2-ethylhexyl (meth)acrylate, vinyl formate, vinyl acetate, 1-methylvinyl acetate, vinyl propionate, vinyl butyrate, vinyl 2-ethylhexanoate, vinyl pivalate, vinyl neodecanoate, and mixtures thereof. As used herein, the term "(meth)acrylic" acid and "(meth)acrylate" are meant to include the corresponding methyl derivatives of acrylic acid and the corresponding alkyl acrylate For example, "(meth)acrylic" acid refers to acrylic acid and/or methacrylic acid and "(meth)acrylate" refers to alkyl acrylate and/or alkyl methacrylate.

The non-crosslinked, linear acrylic copolymer mitigants of the invention can be synthesized via free radical polymerization techniques known in the art. In one aspect of the invention, the amount of the first monomeric component to the second monomeric component utilized ranges from about 20:80 wt. % to about 50:50 wt. %, based on the total weight of all of the monomers in the polymerization medium. In another aspect the weight ratio of the first monomeric component to the second monomeric component is about 35:65 wt. %, and in a further aspect the weight ratio of first monomeric component to second monomeric component is about 25:75 wt. %, all based on the total weight of all monomers in the polymerization medium.

In another aspect emulsion polymerization techniques can be used to synthesize the non-crosslinked, linear acrylic copolymer mitigants of the invention. In a typical emulsion polymerization, a mixture of the disclosed monomers is added with mixing agitation to a solution of emulsifying surfactant, such as, for example, an anionic surfactant (e.g., fatty alcohol sulfates or alkyl sulfonates), in a suitable amount of water, in a suitable reactor, to prepare a monomer emulsion. The emulsion is deoxygenated by any convenient method, such as by sparging with nitrogen, and then a polymerization reaction is initiated by adding a polymerization catalyst (initiator) such as sodium persulfate, or any other suitable addition polymerization catalyst, as is well known in the emulsion polymerization art. The polymerization medium is agitated until the polymerization is complete, typically for a time in the range of about 4 to about 16 hours. The monomer emulsion can be heated to a temperature in the range of about 70 to about 95° C. prior to addition of the initiator, if desired. Unreacted monomer can be eliminated by addition of more catalyst, as is well known in the emulsion polymerization art. The resulting polymer emulsion product can then be discharged from the reactor and packaged for storage or use. Optionally, the pH or other physical and chemical characteristics of the emulsion can be adjusted prior to discharge from the reactor. Typically, the product emulsion has a total solids content in the range of about 10 to about 50 wt. %. Typically, the total polymer content (polymer solids) of the product emulsion is in the range of about 15 to about 45 wt. %, generally not more than about 35 wt. %.

In one aspect, the number average molecular weight ($M_n$) of the linear copolymeric mitigants of the present invention as measured by gel permeation chromatography (GPC) calibrated with a poly(methyl methacrylate) (PMMA) standard is 100,000 or less. In another aspect of the invention, the molecular weight ranges between about 5,000 and about 80,000 $M_n$, in a further aspect between about 10,000 and 50,000 $M_n$, and in a still further aspect between about 15,000 and 40,000 $M_n$.

In one aspect of the invention, the linear copolymeric mitigants have a viscosity of 500 mpa·s or less (Brookfield RVT, 20 rpm, spindle no. 1) at a 5 wt. % polymer solids concentration in deionized water and neutralized to pH 7 with an 18 wt. % NaOH solution. The viscosity can range from about 1 to about 500 mPa·s in another aspect, from about 10 to about 250 mPa·s in a further aspect, and from about 15 to about 150 mPa·s in a still further aspect.

Any of a variety of anionic surfactants may be combined with a polymeric material of the present invention to form a reduced irritation composition according to preferred embodiments of the present methods. According to certain embodiments, suitable anionic surfactants include those selected from the following classes of surfactants: alkyl sulfates, alkyl ether sulfates, alkyl monoglyceryl ether sulfates, alkyl sulfonates, alkylaryl sulfonates, alkyl sulfosuccinates, alkyl ether sulfosuccinates, alkyl sulfosuccinamates, alkyl amidosulfosuccinates, alkyl carboxylates, alkyl amidoethercarboxylates, alkyl succinates, fatty acyl sarcosinates, fatty acyl amino acids, fatty acyl taurates, fatty alkyl sulfoacetates, alkyl phosphates, and mixtures of two or more thereof. Examples of certain preferred anionic surfactants include:

alkyl sulfates of the formula

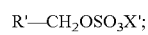

alkyl ether sulfates of the formula

alkyl monoglyceryl ether sulfates of the formula

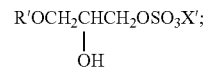

alkyl monoglyceride sulfates of the formula

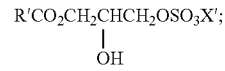

alkyl monoglyceride sulfonates of the formula

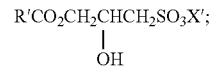

alkyl sulfonates of the formula

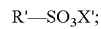

alkylaryl sulfonates of the formula

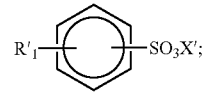

alkyl sulfosuccinates of the formula:

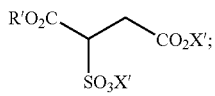

alkyl ether sulfosuccinates of the formula:

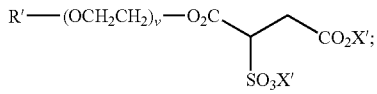

alkyl sulfosuccinamates of the formula:

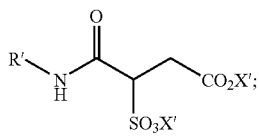

alkyl amidosulfosuccinates of the formula

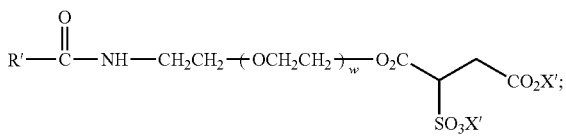

alkyl carboxylates of the formula:

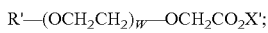

alkyl amidoethercarboxylates of the formula:

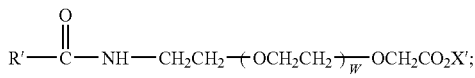

alkyl succinates of the formula:

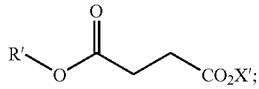

fatty acyl sarcosinates of the formula:

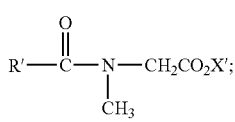

fatty acyl amino acids of the formula:

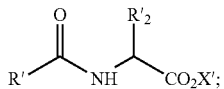

fatty acyl taurates of the formula:

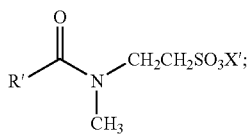

fatty alkyl sulfoacetates of the formula:

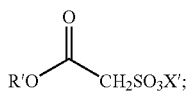

alkyl phosphates of the formula:

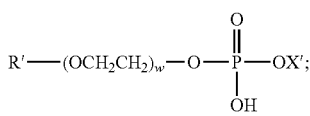

wherein
R' is an alkyl group having from about 7 to about 22, and preferably fom about 7 to about 16 carbon atoms,
R'$_1$ is an alkyl group having from about 1 to about 18, and preferably from about 8 to about 14 carbon atoms,
R'$_2$ is a substituent of a natural or synthetic I-amino acid,
X' is selected from the group consisting of alkali metal ions, alkaline earth metal ions, ammonium ions, and ammonium ions substituted with from about 1 to about 3 substituents, each of the substituents may be the same or different and are selected from the group consisting of alkyl groups having from 1 to 4 carbon atoms and hydroxyalkyl groups having from about 2 to about 4 carbon atoms and
v is an integer from 1 to 6;
w is an integer from 0 to 20;
and mixtures thereof.

According to certain embodiments, the anionic surfactant of the present invention preferably comprises one or more alkyl ether sulfates, or mixtures thereof. In certain more preferred embodiments, the anionic surfactant of the present invention comprises sodium trideceth sulfate. Sodium trideceth sulfate is the sodium salt of sulfated ethoxylated tridecyl alcohol that conforms generally to the following formula, $C_{13}H_{27}(OCH_2CH_2)_nOSO_3Na$, where n has a value between 1 and 4, and is commercially available from Stepan Company of Northfield, Ill. under the tradename, "Cedapal TD-403M."

As used herein, the term "amphoteric" shall mean: 1) molecules that contain both acidic and basic sites such as, for example, an amino acid containing both amino (basic) and acid (e.g., carboxylic acid, acidic) functional groups; or 2) zwitterionic molecules which possess both positive and negative charges within the same molecule. The charges of the latter may be either dependent on or independent of the pH of the composition. Examples of zwitterionic materials include, but are not limited to, alkyl betaines and amidoalkyl betaines. The amphoteric surfactants are disclosed herein without a counter ion. One skilled in the art would readily recognize that under the pH conditions of the compositions of the present invention, the amphoteric surfactants are either electrically neutral by virtue of having balancing positive and negative charges, or they have counter ions such as alkali metal, alkaline earth, or ammonium counter ions.

Examples of amphoteric surfactants suitable for use in the present invention include, but are not limited to, amphocarboxylates such as alkylamphoacetates (mono or di); alkyl betaines; amidoalkyl betaines; amidoalkyl sultaines; amphophosphates; phosphorylated imidazolines such as phosphobetaines and pyrophosphobetaines; carboxyalkyl alkyl polyamines; alkylimino-dipropionates; alkylamphoglycinates (mono or di); alkylamphoproprionates (mono or di),); N-alkyl β-aminoproprionic acids; alkylpolyamino carboxylates; and mixtures thereof.

Examples of suitable amphocarboxylate compounds include those of the formula:

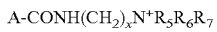

wherein

A is an alkyl or alkenyl group having from about 7 to about 21, e.g. from about 10 to about 16 carbon atoms;

x is an integer of from about 2 to about 6;

$R_5$ is hydrogen or a carboxyalkyl group containing from about 2 to about 3 carbon atoms;

$R_6$ is a hydroxyalkyl group containing from about 2 to about 3 carbon atoms or is a group of the formula:

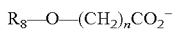

wherein $R_8$ is an alkylene group having from about 2 to about 3 carbon atoms and n is 1 or 2; and $R_7$ is a carboxyalkyl group containing from about 2 to about 3 carbon atoms;

Examples of suitable alkyl betaines include those compounds of the formula:

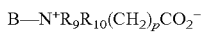

wherein

B is an alkyl or alkenyl group having from about 8 to about 22, e.g., from about 8 to about 16 carbon atoms;

$R_9$ and $R_{10}$ are each independently an alkyl or hydroxyalkyl group having from about 1 to about 4 carbon atoms; and p is 1 or 2.

A preferred betaine for use in the present invention is lauryl betaine, available commercially from Albright & Wilson, Ltd. of West Midlands, United Kingdom as "Empigen BB/J."

Examples of suitable amidoalkyl betaines include those compounds of the formula:

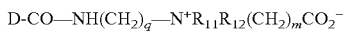

wherein

D is an alkyl or alkenyl group having from about 7 to about 21, e.g. from about 7 to about 15 carbon atoms;

$R_{11}$ and $R_{12}$ are each independently an alkyl or Hydroxyalkyl group having from about 1 to about 4 carbon atoms;

q is an integer from about 2 to about 6; and m is 1 or 2.

One amidoalkyl betaine is cocamidopropyl betaine, available commercially from Goldschmidt Chemical Corporation of Hopewell, Va. under the tradename, "Tegobetaine L7."

Examples of suitable amidoalkyl sultaines include those compounds of the formula

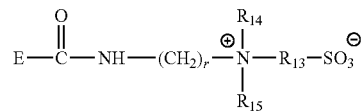

wherein

E is an alkyl or alkenyl group having from about 7 to about 21, e.g. from about 7 to about 15 carbon atoms;

$R_{14}$ and $R_{15}$ are each independently an alkyl, or hydroxyalkyl group having from about 1 to about 4 carbon atoms;

r is an integer from about 2 to about 6; and $R_{13}$ is an alkylene or hydroxyalkylene group having from about 2 to about 3 carbon atoms;

In one embodiment, the amidoalkyl sultaine is cocamidopropyl hydroxysultaine, available commercially from Rhone-Poulenc Inc. of Cranbury, N.J. under the tradename, "Mirataine CBS."

Examples of suitable amphophosphate compounds include those of the formula:

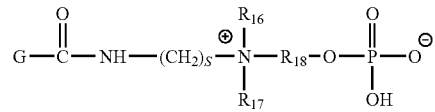

wherein

G is an alkyl or alkenyl group having about 7 to about 21, e.g. from about 7 to about 15 carbon atoms;

s is an integer from about 2 to about 6;

$R_{16}$ is hydrogen or a carboxyalkyl group containing from about 2 to about 3 carbon atoms;

$R_{17}$ is a hydroxyalkyl group containing from about 2 to about 3 carbon atoms or a group of the formula:

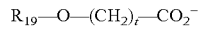

wherein $R_{19}$ is an alkylene or hydroxyalkylene group having from about 2 to about 3 carbon atoms and t is 1 or 2; and $R_{18}$ is an alkylene or hydroxyalkylene group having from about 2 to about 3 carbon atoms.

In one embodiment, the amphophosphate compounds are sodium lauroampho PG-acetate phosphate, available commercially from Mona Industries of Paterson, N.J. under the tradename, "Monateric 1023," and those disclosed in U.S. Pat. No. 4,380,637, which is incorporated herein by reference.

Examples of suitable phosphobetaines include those compounds of the formula:

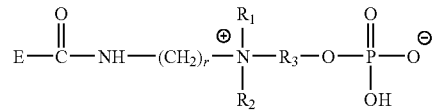

wherein E, r, $R_1$, $R_2$ and $R_3$, are as defined above. In one embodiment, the phosphobetaine compounds are those disclosed in U.S. Pat. Nos. 4,215,064, 4,617,414, and 4,233,192, which are all incorporated herein by reference.

Examples of suitable pyrophosphobetaines include those compounds of the formula:

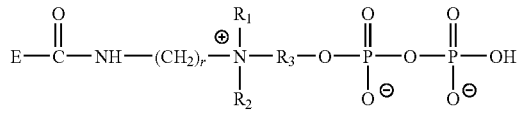

wherein E, r, $R_1$, $R_2$ and $R_3$, are as defined above. In one embodiment, the pyrophosphobetaine compounds are those disclosed in U.S. Pat. Nos. 4,382,036, 4,372,869, and 4,617,414, which are all incorporated herein by reference.

Examples of suitable carboxyalkyl alkylpolyamines include those of the formula:

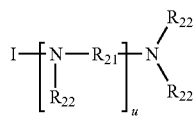

wherein
I is an alkyl or alkenyl group containing from about 8 to about 22, e.g. from about 8 to about 16 carbon atoms;
$R_{22}$ is a carboxyalkyl group having from about 2 to about 3 carbon atoms;
$R_{21}$ is an alkylene group having from about 2 to about 3 carbon atoms and
u is an integer from about 1 to about 4.

Any suitable amounts of polymeric material and surfactants may be used in accord with the present invention. In certain preferred embodiments, the present composition comprise from greater than zero to about 6 weight percent of polymeric material (based on active amount of polymeric material in the total weight of composition). In certain more preferred embodiments, the compositions comprise from about 0.1 to about 4.5 weight percent of polymeric material, more preferably from about 0.3 to about 3.5 weight percent of polymeric material, and even more preferably from about 0.5 to about 2.5 weight percent of polymeric material. In certain preferred embodiments, the present composition comprise from greater than zero to about 30 weight percent of anionic/amphoteric surfactant (based on total active amount of anionic and/or amphoteric surfactant(s) in the total weight of composition). In certain more preferred embodiments, the compositions comprise from about 1 to about 25 weight percent of anionic/amphoteric surfactant, more preferably from about 5 to about 25 weight percent of anionic/amphoteric surfactant, and even more preferably from about 9 to about 20 weight percent of anionic/amphoteric surfactant.

The polymeric material and anionic/amphoteric surfactant may be combined according to the present invention via any conventional methods of combining two or more fluids. For example, one or more compositions comprising, consisting essentially of, or consisting of at least one polymeric material and one or more compositions comprising, consisting essentially of, or consisting of at least one anionic and/or amphoteric surfactant may be combined by pouring, mixing, adding dropwise, pipetting, pumping, and the like, one of the compositions comprising polymeric material or surfactant into or with the other in any order using any conventional equipment such as a mechanically stirred propeller, paddle, and the like.

According to certain embodiments, the combining step comprises combining a composition comprising anionic and/or amphoteric surfactant into or with a composition comprising polymeric material. According to certain other embodiments, the combining step comprises combining a composition comprising polymeric material into or with a composition comprising anionic and/or amphoteric surfactant.

The reduced irritation compositions produced, as well as any of the compositions comprising polymeric material or anionic and/or amphoteric surfactant that are combined in the combining step according to the present methods may further comprise any of a variety of other components nonexclusively including one or more nonionic and/or cationic surfactants, pearlescent or opacifying agents, thickening agents, secondary conditioners, humectants, chelating agents, and additives which enhance the appearance, feel and fragrance of the compositions, such as colorants, fragrances, preservatives, pH adjusting agents, and the like.

Any of a variety of nonionic surfactants are suitable for use in the present invention. Examples of suitable nonionic surfactants include, but are not limited to, fatty alcohol acid or amide ethoxylates, monoglyceride ethoxylates, sorbitan ester ethoxylates alkyl polyglycosides, mixtures thereof, and the like. Certain preferred nonionic surfactants include polyoxyethylene derivatives of polyol esters, wherein the polyoxyethylene derivative of polyol ester (1) is derived from (a) a fatty acid containing from about 8 to about 22, and preferably from about 10 to about 14 carbon atoms, and (b) a polyol selected from sorbitol, sorbitan, glucose, α-methyl glucoside, polyglucose having an average of about 1 to about 3 glucose residues per molecule, glycerine, pentaerythritol and mixtures thereof, (2) contains an average of from about 10 to about 120, and preferably about 20 to about 80 oxyethylene units; and (3) has an average of about 1 to about 3 fatty acid residues per mole of polyoxyethylene derivative of polyol ester. Examples of such preferred polyoxyethylene derivatives of polyol esters include, but are not limited to PEG-80 sorbitan laurate and Polysorbate 20. PEG-80 sorbitan laurate, which is a sorbitan monoester of lauric acid ethoxylated with an average of about 80 moles of ethylene oxide, is available commercially from ICI Surfactants of Wilmington, Del. under the tradename, "Atlas G-4280." Polysorbate 20, which is the laurate monoester of a mixture of sorbitol and sorbitol anhydrides condensed with approximately 20 moles of ethylene oxide, is available commercially from ICI Surfactants of Wilmington, Del. under the tradename "Tween 20."

Another class of suitable nonionic surfactants includes long chain alkyl glucosides or polyglucosides, which are the condensation products of (a) a long chain alcohol containing from about 6 to about 22, and preferably from about 8 to about 14 carbon atoms, with (b) glucose or a glucose-containing polymer. Preferred alkyl gluocosides comprise from about 1 to about 6 glucose residues per molecule of alkyl glucoside. A preferred glucoside is decyl glucoside, which is the condensation product of decyl alcohol with a glucose polymer and is available commercially from Henkel Corporation of Hoboken, N.J. under the tradename, "Plantaren 2000."

Classes of cationic surfactants that are suitable for use in this invention include alkyl quaternaries (mono, di, or tri), benzyl quaternaries, ester quaternaries, ethoxylated quaternaries, alkyl amines, and mixtures thereof, wherein the alkyl group has from about 6 carbon atoms to about 30 carbon atoms, with about 8 to about 22 carbon atoms being preferred.

Any of a variety of commercially available secondary conditioners, such as volatile silicones, which impart additional attributes, such as gloss to the hair are suitable for use in this invention. In one embodiment, the volatile silicone conditioning agent has an atmospheric pressure boiling point less than about 220° C. The volatile silicone conditioner may be present in an amount of from about 0 percent to about 3 percent, e.g. from about 0.25 percent to about 2.5 percent or from about 0.5 percent to about 1.0 percent, based on the overall weight of the composition. Examples of suitable volatile silicones nonexclusively include polydimethylsiloxane, polydimethylcyclosiloxane, hexamethyldisiloxane, cyclomethicone fluids such as polydimethylcyclosiloxane available commercially from Dow Corning Corporation of Midland, Mich. under the tradename, "DC-345" and mixtures thereof, and preferably include cyclomethicone fluids.

Any of a variety of commercially available humectants, which are capable of providing moisturization and conditioning properties to the personal cleansing composition, are suitable for use in the present invention. The humectant may be present in an amount of from about 0 percent to about 10 percent, e.g. from about 0.5 percent to about 5 percent or from about 0.5 percent to about 3 percent, based on the overall weight of the composition. Examples of suitable humectants nonexclusively include: 1) water soluble liquid polyols selected from the group comprising glycerine, propylene glycol, hexylene glycol, butylene glycol, dipropylene glycol, and mixtures thereof; 2) polyalkylene glycol of the formula: HO—(R'O)$_b$—H, wherein R" is an alkylene group having from about 2 to about 3 carbon atoms and b is an integer of from about 2 to about 10; 3) polyethylene glycol ether of methyl glucose of formula $CH_3$—$C_6H_{10}O_5$—$(OCH_2CH_2)_c$—OH, wherein c is an integer from about 5 to about 25; 4) urea; and 5) mixtures thereof, with glycerine being the preferred humectant.

Examples of suitable chelating agents include those which are capable of protecting and preserving the compositions of this invention. Preferably, the chelating agent is ethylenediamine tetracetic acid ("EDTA"), and more preferably is tetrasodium EDTA, available commercially from Dow Chemical Company of Midland, Mich. under the tradename, "Versene 100XL" and is present in an amount, based upon the total weight of the composition, from about 0 to about 0.5 percent or from about 0.05 percent to about 0.25 percent.

Suitable preservatives include Quaternium-15, available commercially as "Dowicil 200" from the Dow Chemical Corporation of Midland, Mich., and are present in the composition in an amount, based upon the total weight of the composition, from about 0 to about 0.2 percent or from about 0.05 percent to about 0.10 percent.

The methods of the present invention may further comprise any of a variety of steps for mixing or introducing one or more of the optional components described hereinabove with or into a composition comprising a polymeric material and/or an anionic and/or amphoteric surfactant either before, after, or simultaneously with the combining step described above. While in certain embodiments, the order of mixing is not critical, it is preferable, in other embodiments, to pre-blend certain components, such as the fragrance and the nonionic surfactant before adding such components into a composition comprising a polymeric material and/or an anionic surfactant.

In certain embodiments, the reduced irritation compositions produced via the present invention are preferably used as or in personal care compositions/products. As used herein, the term "personal care" relates to compositions/products for use on or in the body for cosmetic/health care purposes and the like. For example, personal care products include, but are not limited to, products for use in skin care, infant care, oral care, wound care, sanitary protection, cleansing, women's health, sleep-related products, make-up, cosmetic dermatology, eye care, ear care, nail care, depilatories, hair care, sun protection, anti-aging, anti-acne, and the like. Examples of types of such products may include, but are not limited to, shampoos, washes, baths, gels, lotions, creams, wipes and other applicators, napkins, liners, tampons, bandages, toothbrushes, floss, dental strips, microdermabrasion devices, and the like. As discussed above, applicants have discovered unexpectedly that the instant methods allow for the formulation of such personal care products having reduced irritation to the skin and/or eyes and optionally other combinations of desirable aesthetics.

According to certain other preferred embodiments, the present invention provides methods for treating and/or cleansing a portion of the body, including the skin, hair, teeth, vagina, and the like, preferably the skin or hair, with reduced irritation thereto comprising the step of contacting the body of a mammal with a reduced irritation composition of the present invention.

Any conventional means for contacting the body, preferably mammalian skin and/or hair, can be used according to the present invention. In certain preferred embodiments, the contacting step comprises applying a reduced irritation composition of the present invention to human skin and/or human hair.

The cleansing methods of the present invention may further comprise any of a variety of additional, optional steps associated conventionally with cleansing hair and skin including, for example, lathering, rinsing steps, and the like.

EXAMPLES

The following examples are illustrative of certain embodiments of the present invention and are not intended to be limiting in any manner.

The following Trans-Epithelial Permeability ("TEP"), Tensiometry tests, $M_n$ and $C_{90}$ Measurements are used in the instant methods and in the following Examples.

Trans-Epithelial Permeability Test ("TEP Test"):

Irritation to the eyes and/or skin expected for a given formulation is measured in accordance with the Invittox Protocol Number 86, the "Trans-epithelial Permeability (TEP) Assay" as set forth in Invittox Protocol Number 86 (May 1994), incorporated herein by reference. In general, the ocular and/or skin irritation potential of a product can be evaluated by determining its effect on the permeability of a cell layer, as assessed by the leakage of fluorescein through the layer. Monolayers of Madin-Darby canine kidney (MDCK) cells are grown to confluence on microporous inserts in a 24-well plate containing medium or assay buffer in the lower wells. The irritation potential of a product is evaluated by measuring the damage to the permeability barrier in the cell monolayer following a 15 minute exposure to dilutions of the product. Barrier damage is assessed by the amount of sodium fluorescein that has leaked through to the lower well after 30 minutes, as determined spectrophotometrically. The fluorescein leakage is plotted against the concentration of test material to determine the $EC_{50}$ (the concentration of test material that causes 50% of maximum dye leakage, i.e., 50% damage to the permeability barrier). Higher scores are indicative of milder formulas.

Exposure of a layer of MDCK cells grown on a microporous membrane to a test sample is a model for the first event that occurs when an irritant comes in contact with the eye. In vivo, the outermost layers of the corneal epithelium form a selectively permeable barrier due to the presence of tight junctions between cells. On exposure to an irritant, the tight junctions separate, thereby removing the permeability barrier. Fluid is imbibed to the underlying layers of epithelium and to the stroma, causing the collagen lamellae to separate, resulting in opacity. The TEP assay measures the effect of an irritant on the breakdown of tight junctions between cells in a layer of MDCK cells grown on a microporous insert. Damage is evaluated spectrophotometrically, by measuring the amount of marker dye (sodium fluorescein) that leaks through the cell layer and microporous membrane to the lower well.

Tensiometry Titration Test:

A well-known method to measure the surface tension of surfactant solutions is the Wilhelmy plate method (Holmberg, K.; Jonsson, B.; Kronberg, B.; Lindman, B. *Surfactants and Polymers in Aqueous Solution*, Wiley & Sons, p. 347). In the method, a plate is submerged into a liquid and the downward force exerted by of the liquid on the plate is measured. The surface tension of the liquid can then be determined based on the force on the plate and the dimensions of the plate. It is also well known that by measuring the surface tension over a range of concentrations the critical micelle concentration (CMC) can then be determined.

There are commercially available Wilhelmy plate method instruments. In the following examples, a Kruss K12 Tensiomter (Kruss USA, Mathews, N.C.) with a platinum Wilhelmy plate used to determine the surface tension of each sample over a range of concentrations. The test can be run either forward or reverse. In either case, a sample vessel contains some initial solution in which the Wilhelmy plate measures the surface tension. Then a second solution is dosed into the sample vessel, stirred, and then probed again with the Wilhelmy plate. The solution initially in the sample vessel before the titration begins, into which the second solution is dosed, will be referred to hereinafter as the initial solution, and the solution that is dosed into the sample vessel during the titration will be referred to hereinafter as the dosing solution, in accordance with the convention used by Kruss USA.

In the forward titration, the concentration of the initial solution is lower than the concentration of the dosing solution. During forward titration tests, the initial solution was HLPC grade water (Fischer Scientific, N.J.), with no surfactant. The dosing solution was a solution of surfactant to be associated with the polymer and HLPC grade water (Fischer Scientific, N.J.) with a concentration of 5750 mg/L of surfactant. A large stock solution, 4 L, of the dosing surfactant solution was prepared before hand; the surfactant was added to HLPC grade water (Fischer Scientific, N.J.) to a concentration of 5750 mg/L.

At the beginning of the forward titration, 30 ml of initial solution was added to the sample vessel. The surface tension of this initial solution was measured, and then a volume of the dosing solution was added to the sample vessel. The solution was stirred for at least 5 minutes, before the next surface tension measures was taken. At least forty volumes of dosing solution are added and the surface tension measured after addition. All titrations were run from 0 mg/L to at least 3500 mg/L of the surfactant. A test run according to this procedure is here after referred to as a Forward Titration Tensiomtry Test.

Alternatively in the reverse titration, the concentration of the initial solution is higher than the concentration of the dosing solution. During the reverse titration tests, the dosing solution is HLPC grade water (Fischer Scientific, N.J.), with no surfactant, 0 mg/L. The full concentration formulas are diluted with HLPC grade water (Fischer Scientific, N.J.) to a dilution of approximately 5% wt. This 5% diluted solution is then added to the sample vessel and is the initial solution. The surface tension of this initial solution is measured, and then a 30 ml volume of the dosing solution is added to the sample vessel. The solution was stirred for at least 5 minutes, before the next surface tension measures is taken. This dosing, stirring, and then measuring was repeated until the dilution reached at least 0.0008%. A Test run according to this procedure is here after referred to as a Reverse Titration Tensiomtry Test.

Figure 3:
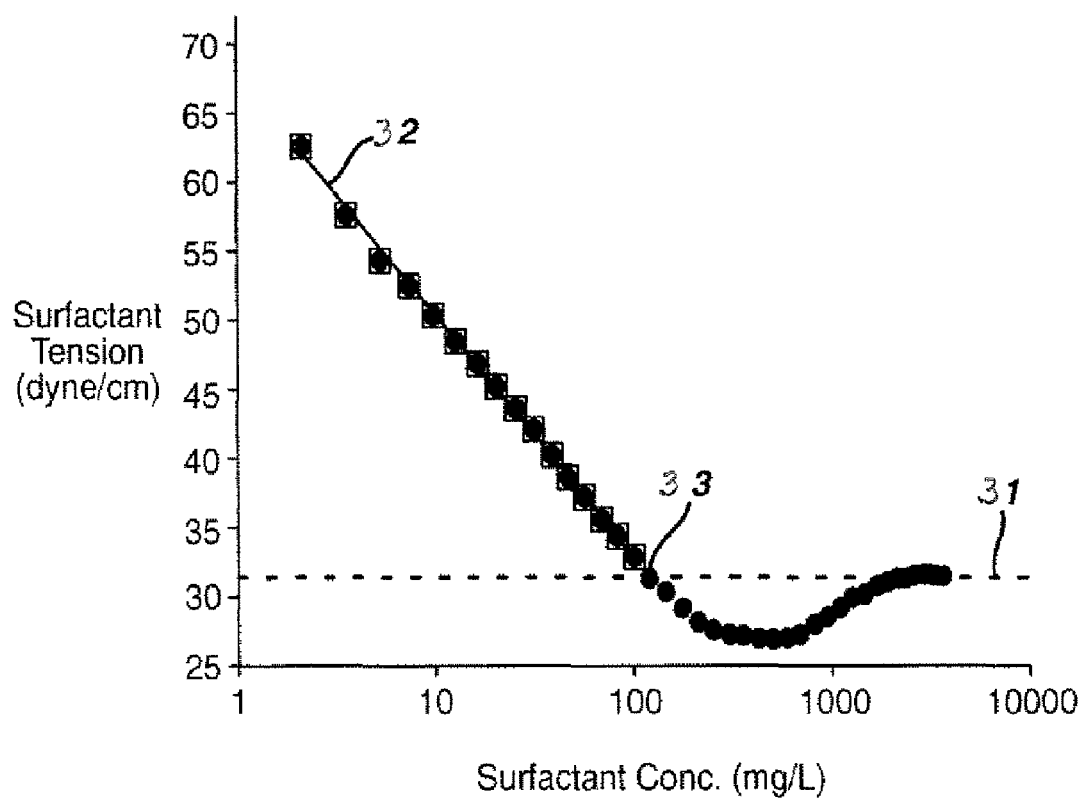
FIG. 3 is a graphical depiction of the tensiometry data associated with a composition of the present invention.

From the raw tensiomtry data, the CMC was determined for each sample in the following manner. First, the equation for a horizontal line was fitted to the portion of the data at high concentrations, i.e. concentrations above the nadir of the graph and well into the region where the surface tension is essentially constant, as shown, for example, in FIG. 3 as line 31. Then, the equation for a straight line is fit to the data at lower concentrations having a surface tension above the horizontal line derived previously, as shown, for example, in FIG. 3 as line 32. The intersection of these two lines/equations 33 was then defined as the CMC for that sample.

$C_{90}$ Measurements

The $C_{90}$ attributed to a polymer for associating a surfactant thereto is calculated as follows. Eight compositions comprising the polymer in HPLC grade water at concentrations (in mg/L) of: 0, 50, 100, 175, 250, 375, 500 and 750 are prepared. The CMC associated with each composition with a particular surfactant are calculated via the Forward Tensiometry Titration test. The Delta CMC for each of the compositions comprising polymer are then calculated using such data. Based on such Delta CMC data and/or graphical representation of the Delta CMCs as a function of polymer concentration fit with an appropriate curve, the lowest concentration polymer composition which exhibits a Delta CMC value that is 90% of the Delta CMC value of the polymer composition having a concentration of 750 mg/L is determined, and such concentration value represents the $C_{90}$ value for such polymer and surfactant combination. Reference is made, for example, to the procedure in Example 1.

Molecular Weight Determination

The number average ($M_n$) of the polymer samples are determined via the GPC method using a PL-220 high temperature GPC instrument manufactured by Polymer Laboratories. The instrument is integrated with a Compaq Dell OptiPlex GX270 computer with Waters Empower Pro LC/GPC software. Approximately 0.02 g polymer sample is dissolved in 5 ml of dimethyl actamide (DMAc), containing 250 ppm BHT and 0.05 molar $NaNO_3$. The test sample solution is gently shaken for about two hours and filtered with a 0.45 μm PTFE disposable disc filter. The chromatographic conditions are:

| | |
|---|---|
| Mobile phase: | DMAc, with 250 ppm BHT and 0.05 m $NaNO_3$, 70° C., 1.0 ml/min. |
| Sample size: | 100 μl |
| Column set: | PLgel (Guard + 2 x Mixed-B), all 10 μm, in series |
| Detector: | Refractive Index Detector |
| Calibration standard: | PMMA |

Example 1

The following example illustrates the efficiency of certain polymers of the present invention to associate surfactant thereto and reduce irritation as compared to higher molecular weight polymeric materials.

Compositions (E1-E5) comprising a non-crosslinked, linear acrylic copolymer derived from methacrylic acid and ethyl acrylate, wherein the methacrylic acid:ethyl acrylate ratio is about 25:75% %, based on the total weight of all of the monomers in the polymerization medium and having a $M_n$ of from about 15,000 to about 40,000 from Noveon, Inc. ("Ex. 968") in water, and comparable compositions comprising no polymer (C1), higher molecular weight polymers (C2-C8), and comparable low molecular weight polymer (C9-C15) were prepared as described below. The CMCs, Delta CMCs, and Delta CMC/750 for each composition with surfactant sodium trideceth sulfate (TDES) were calculated using the Forward Titration Tensiomtry Test as described herein and the results reported in Table 2.

TABLE 1*

| Trade name | INCI Name | E1 | E2 | E3 | E4 | E5 |
|---|---|---|---|---|---|---|
| Ex. 968 | | 0.010 | 0.025 | 0.035 | 0.050 | 0.075 |
| Sodium Hydroxide solution (20%) | Sodium Hydroxide | — | — | — | — | — |
| DI Water | DI Water | Qs | Qs | Qs | Qs | Qs |

| Trade name | INCI Name | C1 | C2 | C3 | C4 | C5 | C6 | C7 | C8 |
|---|---|---|---|---|---|---|---|---|---|
| Carbopol AQUA SF1 (30%) | Acrylates Copolymer | — | 0.005 | 0.010 | 0.015 | 0.025 | 0.0375 | 0.050 | 0.075 |
| Sodium Hydroxide solution (20%) | Sodium Hydroxide | As needed | As needed | As needed | As needed | As needed | As needed | As needed | As needed |
| DI Water | DI Water | Qs | Qs | Qs | Qs | Qs | Qs | Qs | qs |

| Trade name | INCI Name | C9 | C10 | C11 | C12 | C13 | C14 | C15 |
|---|---|---|---|---|---|---|---|---|
| Inutec SP-1 | Inulin Lauryl Carbamate | 0.005 | 0.010 | 0.0175 | 0.025 | 0.0375 | 0.050 | 0.075 |
| Sodium Hydroxide (20%) | Sodium Hydroxide | — | — | — | — | — | — | — |
| DI Water | DI Water | Qs | Qs | Qs | Qs | Qs | Qs | qs |

*expressed in % W/W

The compositions of Table 1 were prepared as follows: HPLC grade water (50.0 parts) was added to a beaker. The polymer, if any, was added to the water with mixing. For the solutions containing Carbopol Aqua SF-1, the pH of each resulting solution was then adjusted with a 20% Sodium Hydroxide solution (as needed) until a final pH of about 7.0 was obtained. The remainder of the water was then added thereto.

The compositions of Table 1 were tested for Critical Micelle Concentration (CMC) values using the Forward Titration Tensiomtry Test. The Delta CMCs for each composition were calculated based on the CMC for comparable composition C1 and such values were plotted as a function of polymer concentration in FIG. 1 as an illustration of the efficiency of the polymers to associate surfactant thereto (and reduce irritation).

TABLE 2

| Examples | Ex. 968 (mg/L) | CMC TDES (mg/L) | Δ CMC TDES (mg/L) | Efficiency | Δ CMC/750 % |
|---|---|---|---|---|---|
| | 0 | 136 | na | na | na |
| E1 | 100 | 269 | 133 | 1.3 | 35 |
| E2 | 250 | 362 | 226 | 0.9 | 59 |
| E3 | 350 | 386 | 250 | 0.7 | 66 |
| E4 | 500 | 454 | 318 | 0.6 | 83 |
| E5 | 750 | 517 | 381 | 0.5 | 100 |

| Examples | Aqua SF-1 (mg/L) | CMC TDES (mg/L) | Δ CMC TDES (mg/L) | Efficiency | Δ CMC/750 % |
|---|---|---|---|---|---|
| C1 | 0 | 136 | na | na | na |
| C2 | 50 | 213 | 77 | 1.5 | 26 |
| C3 | 100 | 291 | 155 | 1.6 | 52 |
| C4 | 150 | 328 | 192 | 1.3 | 64 |
| C5 | 250 | 410 | 274 | 1.1 | 92 |
| C6 | 375 | 468 | 332 | 0.9 | 111 |
| C7 | 500 | 431 | 295 | 0.6 | 99 |
| C8 | 750 | 434 | 298 | 0.4 | 100 |

| Composition | Inutec SP-1 (mg/L) | CMC TDES (mg/L) | Δ CMC TDES (mg/L) | Efficiency | Δ CMC/750 % |
|---|---|---|---|---|---|
| C1 | 0 | 136 | na | na | na |
| C9 | 50 | 182 | 46 | 0.9 | 7 |
| C10 | 100 | 258 | 122 | 1.2 | 18 |
| C11 | 175 | 370 | 234 | 1.3 | 34 |
| C12 | 250 | 452 | 316 | 1.3 | 46 |
| C13 | 375 | 595 | 459 | 1.2 | 66 |
| C14 | 500 | 777 | 641 | 1.3 | 92 |
| C15 | 750 | 830 | 694 | 0.9 | 100 |

Also shown in Table 2 for each of the compositions is the Efficiency, which is defined herein as the ratio of the Delta CMC (mg/L) to the polymer concentration. The Efficiency is a measure of how much surfactant the polymer associates at a given concentration.

To better assess the differences between the polymers in efficiency as a function of polymer concentration also shown in Table 2 is ΔCMC/750, which is defined herein as the ratio of the ΔCMC at a particular concentration to the ΔCMC of a composition having a polymer concentration of 750 mg/L (times 100 to get a % value). The ΔCMC/750 provides a metric of the extent to which the polymer tends to lose efficiency as concentration of the polymer is increased. For instance Aqua SF-1 reaches a ΔCMC/750 of 92% at a polymer concentration of only about 250 ml/L, while Inutec SP-1 does not reach a ΔCMC/750 of 92% until a polymer concentration of about 500 mg/L. This suggests that while a polymer concentration of Aqua SF-1 above 250 mg/L tends to provide relatively little additional TDES association, Inutec SP-1 is capable of associating relatively significant amounts of additional surfactant at concentrations greater than 500 mg/L. The "$C_{90}$ value" of a polymer and surfactant combination is the lowest polymer concentration at which the ΔCMC/750 of compositions comprising the polymer and surfactant, as measured via the Forward Titration Tensiomtry Test as described hereinabove, is equal to 90%. As shown above, the $C_{90}$ value associated with the comparable SF-1 polymer and TDES is less than about 250 mg/L, while the Inutec SP-1 polymer and TDES is greater than about 250 mg/L (about 500 mg/L) and the $C_{90}$ value associated with Ex. 968 and TDES is greater than about 250 mg/L (and greater than about 500 mg/L).

Example 2

The following example illustrates the efficiency of certain polymers of the present invention to associate surfactant thereto and reduce irritation as compared to other low molecular weight polymeric materials.

The CMCs, Delta CMCs, Efficiency, Delta CMC/750, and $C_{90}$ for Compositions (E1-5) and comparable compositions comprising a low molecular weight octadecene/maleic anhydride copolymer designated "PA-18" with the surfactant cocamidopropyl betaine (CAPB) were calculated using the Forward Titration Tensiomtry Test as described below and the results reported in Table 3.

The compositions were tested for Critical Micelle Concentration (CMC) values using the Forward Titration Tensiomtry Test. The Delta CMCs for each composition were calculated based on the CMC for comparable composition C1.

TABLE 3

| Examples | | CMC CAPB (mg/L) | Δ CMC CAPB (mg/L) | Efficiency | Δ CMC/750 CAPB % |
|---|---|---|---|---|---|
| | Ex. 968 (mg/L) | | | | |
| C1 | 0 | | na | na | Na |
| E1 | 50 | 191 | 174 | 3.5 | 6 |
| E2 | 250 | 920 | 903 | 3.6 | 34 |
| E3 | | | | | |

TABLE 3-continued

| Examples | | CMC CAPB (mg/L) | Δ CMC CAPB (mg/L) | Efficiency | Δ CMC/750 CAPB % |
|---|---|---|---|---|---|
| E4 | 500 | 1522 | 1505 | 3.0 | 56 |
| E5 | 750 | 2698 | 2681 | 3.6 | 100 |
| | PA-18 (mg/L) | | | | |
| C1 | 0 | | na | na | Na |
| C16 | 50 | 309 | 254 | 5.1 | 11 |
| C17 | 250 | 1225 | 1128 | 4.5 | 48 |
| C18 | 350 | 1611 | 1481 | 4.2 | 63 |
| C19 | 500 | 2100 | 1905 | 3.8 | 82 |
| C20 | 750 | 2675 | 2333 | 3.1 | 100 |

As shown in Table 3, the $C_{90}$ value associated with the Ex. 968 polymer and CAPB is greater than about 250 mg/L (and greater than 500 mg/L).

Example 3

The following example illustrates the significant clarity associated with compositions of certain embodiments of the present invention as compared to other comparable compositions comprising other low molecular weight polymeric materials and high molecular weight polymeric materials.

Composition E6 in accord with the present invention and comparative compositions C21-C23 were prepared and the clarity measured for each composition.

TABLE 4

| Trade Name | INCI name | C21 w/w % | C22 w/w % | E6 w/w % | C23 w/w % |
|---|---|---|---|---|---|
| Cedepal TD-403 (30%) | Sodium trideceth sulfate | 9.00 | 9.00 | 9.00 | 9.00 |
| Tegobetaine L-7V | Cocamidopropyl betaine | 9.00 | 9.00 | 9.00 | 9.00 |
| Merquat S | Polyquaternium-7 | 0.14 | 0.14 | 0.14 | 0.14 |
| Versene 100 XL | Tetrasodium EDTA | 0.10 | 0.10 | 0.10 | 0.10 |
| Aqua SF-1 (30%) | Acrylates copolymer | — | 6.00 | — | — |
| Ex-968 (30%) | Acrylates copolymer (low Mw) | — | — | 6.00 | — |
| Inutec SP-1 | Inulin Lauryl Carbamate | — | — | — | 1.8 |
| 20% NaOH | Sodium hydroxide | qs | qs | qs | qs |
| Deionized water | Water | qs | qs | qs | qs |

*expressed in % W/W

Each of the compositions of Table 4 was independently prepared as follows: Water (50.0 parts) was added to a beaker. The following ingredients were then added thereto independently with mixing until each respective resulting mixture was homogenous: Ex. 968, Aqua SF-1 or Inutec SP-1 (depending on the example), Cedepal TD403MF-D, Tegobetaine L7-V, Merquat S, Versene 100XL, and Nipasept. The pH of the resulting solution was then adjusted with a 20% solution of Citric Acid of Sodium hydroxide solution until a final pH of about 6.3 to 6.6 was obtained. The remainder of the water was then added thereto.

The clarity of each sample was measured via the Clarity Test, the procedure for which comprises preparing a 1 cm cell sample of the composition to be measured and measuring the % light transmittance associated with such sample using a Agilent 8453 UV-Visible Spectrophotometer with a 1 cm cell at a wavelength of 800 nm. The results are shown in Table 5.

TABLE 5

| Example | Polymer added | Clarity (% transmitance) |
|---|---|---|
| C21 | No polymer | 99.1 ± 0.2 |
| E6 | Ex-968 | 98.8 ± 0.1 |
| C22 | Aqua SF-1 | 88.3 ± 0.2 |
| C23 | Inutec SP-1 | 37.1 ± 0.9 |

Example 4

This example further illustrates the clarity associated with compositions of the present invention as compared to comparable compositions comprising other low molecular weight polymers and/or high molecular weight polymers.

The turbidity associated with five commercial cleansing products was measured using the Turbidity test as follows: the turbidity of a surfactant containing composition was determined in Nephelometric Turbidity Units (NTU) employing a nephelometric turbidity meter (Mircro 100 Turbidimeter, HF Scientific, Inc.) with distilled water (NTU=0) as the standard. Six dram screw cap vials (70 mm×25 mm) are filled almost to the top with test sample and centrifuged at 100 rpm until all bubbles are removed. Upon centrifugation each sample vial is wiped with tissue paper to remove any smudges before placement in the turbidity meter. The sample is placed in the turbidity meter and a reading is taken. Once the reading stabilizes the NTU value is recorded. The vial is given one-quarter turn and another reading is taken and recorded. This is repeated until four readings are taken. The lowest of the four readings is reported as the turbidity value. Compositions having an NTU value of about 90 or greater were judged turbid.

The five commercial products were as follows: Johnson's Baby Shampoo (JBS) which contains the ingredients as listed on the label (Water, PEG-80 Sorbitan Laurate, Cocamidopropyl Betaine, Sodium Trideceth Sulfate, Glycerin, Lauroamphoglycinate, PEG-150 Distearate, Sodium Laureth-13 Carboxylate, Fragrance, Polyquaternium-10, Tetrasodium EDTA, Quaternium-15, Citric Acid, D&C Yellow 10); Johnson's Baby Shampoo Detangling (JBS Detangling) which contains the ingredients as listed on the label (Water, Cocamidopropyl Betaine, PEG-80 Sorbitan Laurate, Sodium Trideceth Sulfate, PEG 150 Distearate, Fragrance, Polyquaternium-10, Tetrasodium EDTA, Quaternium-15, Citric Acid, FD&C Red 40, D&C Yellow 10; Johnson's Baby Shampoo with Natural Lavender (JBS Lavender) which contains the ingredients as listed on the label, (Water, PEG-80 Sorbitan Laurate, Cocamidopropyl Betaine, Sodium Trideceth Sulfate, Glycerin, Disodium Lauroamphodiacetate, PEG 150 Distearate, Sodium Laureth 13 Carboxylate, Fragrance (Lavender & Chamomile), Polyquaternium-10, Tetrasodium EDTA, Quaternium-15, Ext D&C Violet 2); Johnson's Head-to-Toe Body Wash (HTT) which contains the ingredients as listed on the label (Water/Eau, Cocamidopropyl Betaine, PEG-80 Sorbitan Laurate, Sodium Laureth Sulfate, PEG-150 Distearate, Tetrasodium EDTA, Sodium Chloride, Polyquaternium-10, Fragrance, Quatermium-15, Citric Acid); and Johnson's Kids Head-to-Toe Body Wash Berry Breeze (Johnson's Kids) which contains the ingredients as listed on the label (Water, PEG-80 Sorbitan Laurate, Cocamidopropyl Betaine, Sodium Trideceth Sulfate, Glycerin, PEG 150 Distearate, Disodium Lauroamphodiacetate, Sodium Laureth 13 Carboxylate, Fragrance, Polyquaternium-10, Tetrasodium EDTA, Quaternium-15, FD&C Red 40, D&C Red 33).

Six gram samples of Ex. 968 and SF-1 were independently added to 94 gram samples of each of the five commercial products and the turbidity associated with each new composition measured via the Turbidity test. The results of all such measurements is shown in Table 6.

TABLE 6

| Base | Polymer added | Turbidity (NTU) |
|---|---|---|
| JBS | No polymer | 2.2 |
| JBS | Ex-968 | 5.6 |
| JBS | Aqua SF-1 | 133 |
| JBS Detangling | No polymer | 1.0 |
| JBS Detangling | Ex-968 | 4.0 |
| JBS Detangling | Aqua SF-1 | 27 |
| JBS Lavender | No polymer | 2.0 |
| JBS Lavender | Ex-968 | 2.0 |
| JBS Lavender | Aqua SF-1 | 355 |
| Johnson's Kids | No polymer | 0.0 |
| Johnson's Kids | Ex-968 | 4.0 |
| Johnson's Kids | Aqua SF-1 | 550 |
| HTT | No polymer | 0.0 |
| HTT | Ex-968 | 0.0 |
| HTT | Aqua SF-1 | 520 |

As seen in Table 5, example C21 (without any polymer) and Example E6 (with Ex. 968) had excellent clarity with 99.1% and 98.8 transmittance, respectively. While Examples C22 (with Aqua SF-1) and C23 (with Inutec SP-1) were observed to be significantly less clear. These results are further confirmed as shown in Table 6. The polymer Ex. 968 has excellent clarity (low turbidity) when added to a variety of clear bases (comparable to the clear formula without any additional polymer), while Aqua SF-1 has significantly poorer clarity (higher turbidity). While all three polymers (Aqua SF-1, Inutec SP-1 and Ex. 968) tended to provide irritation mitigation, only Ex. 968 tended to provide a clear formula.

Example 5

This example further illustrates the relatively low irritation associated with compositions of the present invention according to certain embodiments.

TABLE 7

| Trade Name | INCI name | Ex. AA w/w % | Ex. BB w/w % |
|---|---|---|---|
| Ex 968 (30%) | Acrylates copolymer | 6.000 | 7.5 |
| Cedepal TD-403 (30%) | Sodium trideceth sulfate | 16.000 | 16.000 |
| Tegobetaine L-7V (30%) | Cocamidopropyl betaine | 22.500 | 22.500 |
| Altas G-4280 (70%) | PEG-80 Sorbitan laurate | 2.000 | 2.000 |
| Versene 100 XL | Tetrasodium EDTA | 0.250 | 0.250 |
| Promidium LTS | PEG 150 Disetearate & PPG-2 Hydroxyethyl Cocamide | 0.750 | 0.750 |
| Fragrance TAH 23194 | Frangrance | 0.275 | 0.275 |
| Tween 20 | Polysorbate 20 | 0.500 | 0.500 |
| Celquat 230M | Polyquaternium 10 | 0.1425 | 0.1425 |
| Versene 100 XL | Tetrasodium EDTA | 0.250 | 0.250 |
| Sharomix 824 | Phenoxyethanol & parabens | 0.600 | 0.600 |
| Yellow #10 (0.1% solution) | FD&C Yellow #10 | 0.240 | 0.240 |
| Orange #4 (0.1% solution) | FD&C Orange #4 | 0.220 | 0.220 |
| 20% NaOH | Sodium hydroxide | qs | qs |
| Deionized water | Water | qs | qs |

TABLE 8

| Example | Ex. 968 added | TEP |
|---|---|---|
| Example AA | 6.0% | 2.9 |
| Example BB | 7.5% | 3.5 |

Compositions AA and BB are made in accord with the amounts in Table 7. As seen in Table 8, Example AA (with Ex. 968 at 7.5 wt %) has a significantly higher TEP score than Example BB (with Ex. 968 at 7.5 wt %). Even at polymer levels above 6.0 wt %, increased levels of Ex. 968 results in significant improvement in the mildness of the formula.

We claim:

1. A personal care composition comprising a low molecular weight, non-crosslinked, linear acrylic copolymer derived from at least one first monomeric component selected from the group consisting of (meth)acrylic acid and at least one second monomeric component selected from the group consisting of one or more $C_1$ to $C_9$ alkyl (meth)acrylates, and at least one surfactant selected from the group consisting of anionic surfactants, amphoteric surfactants, nonionic surfactants and combinations of two or more thereof, wherein said composition comprises from 0.025 to about 4.5 weight percent of said low molecular weight copolymer and said low molecular weight copolymer has a number average molecular weight of about 100,000 or less.

2. The composition of claim 1 having a clarity of at least about 90% transmittance.

3. The composition of claim 1 having a clarity of at least about 95% transmittance.

4. The composition of claim 1 having a turbidity of less than about 20 NTU.

5. The composition of claim 1 having a turbidity of less than about 10 NTU.

6. The composition of claim 1 wherein said copolymer and said at least one surfactant exhibit a $C_{90}$ that is greater than about 250 mg/L.

7. The composition of claim 1 wherein said copolymer and said at least one surfactant exhibit a $C_{90}$ that is greater than about 500 mg/L.

8. The composition of claim 1 wherein said copolymer has a number average molecular weight of from about 5,000 to about 80,000.

9. The composition of claim 1 wherein said copolymer has a number average molecular weight of from about 10,000 to about 50,000.

10. The composition of claim 1 wherein said copolymer has a viscosity of 500 mPa·s or less at a 5 wt. % polymer solids concentration in deionized water and neutralized to pH 7 with an 18 wt. % NaOH solution.

11. The composition of claim 1 wherein said second monomeric component is selected from the group consisting of ethyl (meth)acrylate, butyl (meth)acrylate, 2-ethylhexyl (meth)acrylate, vinyl acetate, 1-methylvinyl acetate, vinyl propionate, vinyl butyrate, vinyl 2-ethylhexanoate, vinyl pivalate, vinyl neodecanoate, and mixtures of two or more thereof.

12. The composition of claim 1 wherein the ratio of said first monomer component to said second monomer component ranges from about 20:80 wt. % to about 50:50 (wt./wt.) based on the total weight of the monomers in the polymerization medium.

13. The personal care product of claim 1 wherein said product is selected from the group consisting of shampoos, washes, baths, gels, lotions, creams, wipes, and combinations of two or more thereof 14. A method of cleansing at least a portion of the human body comprising applying a composition of claim 1 to the body.

15. The composition of claim 1 wherein said composition comprises from about 0.1 to about 4.5 active weight percent of said low molecular weight copolymer.

16. The composition of claim 15 wherein said second monomeric component comprises ethyl acrylate.

* * * * *